United States Patent [19]

Glatt

[11] Patent Number: 4,854,160

[45] Date of Patent: Aug. 8, 1989

[54] EQUILIBRIUM AND AMBIENT RELATIVE HUMIDITY INDICATOR

[76] Inventor: Otto G. Glatt, 18 Mary Dr., Towaco, N.J. 07082

[21] Appl. No.: 146,855

[22] Filed: Jan. 22, 1988

Related U.S. Application Data

[63] Continuation-in-part of Ser. No. 8,479, Jan. 29, 1987, abandoned.

[51] Int. Cl.4 .................. G01N 25/56; G01W 1/02
[52] U.S. Cl. .................................... 73/73; 73/336; 235/89 R; 374/142
[58] Field of Search .................. 73/73, 336, 431; 374/134, 17, 142, 19, 27, 28; 235/89 R

[56] References Cited

U.S. PATENT DOCUMENTS

| | | | |
|---|---|---|---|
| 1,162,446 | 11/1915 | Bristol | 73/336 |
| 2,249,867 | 7/1941 | Snelling | 73/335 |
| 2,799,167 | 7/1957 | Loconti | 374/162 |
| 3,214,975 | 11/1965 | Solecki | 73/336 |
| 3,704,625 | 12/1972 | Seto et al. | 374/162 |
| 4,034,609 | 7/1977 | Fuller | 73/335 |
| 4,150,570 | 4/1979 | Fuller . | |
| 4,154,104 | 5/1979 | Worthington | 73/336 |
| 4,464,064 | 8/1984 | D'Luzansky . | |
| 4,538,926 | 9/1985 | Chretien | 374/162 |

Primary Examiner—Daniel M. Yasich
Attorney, Agent, or Firm—Weingram & Zall

[57] ABSTRACT

A temperature and humidity indicator is provided by a plurality of liquid crystals sensitive to different temperatures which form a graduated scale and a plurality of paper segments impregnated with an inorganic salt sensitive to humidity forming a second graduated scale on a supporting sheet. The crystals change color with temperature and the paper segments change color with humidity. The two scales provide the vertical and horizontal axes of a table of equilibrium relative humidity and ambient relative humidity values for paper sheets or rolls to be printed on and the air surrounding the sheets. Readings are taken from the table to determine the differences in himidity between the air and paper. A second parameter table indicates ranges of differences which should not be exceeded under various printing conditions in order to prevent the occurrence of printing problems.

10 Claims, 2 Drawing Sheets

EQUILIBRIUM AND AMBIENT RELATIVE HUMIDITY INDICATOR

This application is a continuation-in-part of copending application Ser. No. 008,479, filed Jan. 29, 1987, now abandoned.

BACKGROUND OF THE INVENTION

1. Field of the Invention

The present invention relates to a temperature and a humidity sensing indicator used as a hygrometer for monitoring equilibrium relative humidity (ERH) of stacked paper sheets and the ambient relative humidity (ARH) of the surrounding air. The measurements are correlated on a table with the difference in relative humidity readings determining the conditions for printing on the paper.

2. Description of the Prior Art

The moisture content of paper influences its physical properties and produces dimensional variations which effect the printing conditions. It is important for the printer to know the temperature and humidity of the air surrounding the paper as well as the equilibrium relative humidity of the paper sheets or rolls. Present devices for measuring these properties include mechanical and electronic devices such as sword probes which can be inserted into the paper stacks to measure the temperature and relative humidity of the paper. These devices are quite expensive, cumbersome and do not provide a simple way to measure ambient relative humidity and for correlating the readings to determine the difference and the effect on printing conditions. Efforts to minimize the difference between ambient relative humidity and the paper ERH include the use of plastic covers for the paper to maintain the desired conditions before printing and temperature and humidity controls for the ambient air. However, there has been no simplified tabular guide to indicate a safe range of operating conditions and a range of allowable differences in moisture for different printing conditions.

Known methods for indicating temperature include liquid crystal devices which change color with temperature, such as described in U.S. Pat. Nos. 4,464,064 and 4,034,609, while humidity sensing devices include paper impregnated with inorganic salt compositions which change color with humidity, such as described in U.S. Pat. No. 4,150,570. These known devices however have not been utilized together to provide a simplified temperature and humidity sensor which can be employed to obtain both ambient relative humidity and equilibrium relative humidity readings for monitoring paper printing conditions.

SUMMARY OF THE INVENTION

It is therefore the primary object of the present invention to provide a simple inexpensive device for determining the equilibrium relative humidity (ERH) of stacked sheets or rolls of paper and the ambient relative humidity (ARH) of the surrounding air for monitoring printing conditions.

Another object of the invention is to provide simple inexpensive temperature and humidity sensors which can be employed to obtain readings of ERH and ARH in tabular form.

A further object of the invention is to provide a compact easy to use temperature and humidity indicator which can be inserted into a stack or roll of paper to be printed upon to obtain a reading of ERH and can also determine the ARH of the surrounding air.

An additional object is to provide thin flat temperature and humidity sensing scales on a common supporting sheet for insertion into a paper stack to measure the ERH and to measure the ARH of the surrounding air.

It is also an object of the invention to provide a table of ERH and ARH readings which are extrapolated from the temperature an humidity scales so that each combination of temperature and percent humidity represents a predetermined relative humidity reading.

A still further object is to provide another table indicating a range of differences between ERH and ARH for determining the effect on printing conditions.

Yet another object of the invention is to provide a tabular guide with directions for use to indicate a safe range of relative humidity readings for different temperature and percent humidity conditions and a range of allowable differences between ERH and ARH under various printing conditions and corrective measures to be taken when problems occur.

These objects are achieved in a preferred embodiment which utilizes a linear array of temperature sensitive encapsulated thin flat liquid crystals each having a color which varies with room temperature. The crystals are applied in discrete areas to a flexible sheet of plastic or paper, with each area selected to brighten at a particular temperature which is imprinted on the crystal covering to provide a graduated scale of crystal indicators. Colors change from dark gray or black through deep blue to a light shade of green and brown and back to black. One of the crystals brightens to a light color at the room temperature to which it is sensitive. A second linear strip of discrete paper sections impregnated with inorganic salt compositions which change color with humidity is secured adjacent to the temperature scale along the same sheet. The colors vary from bright blue to light blue, lavender and pink with increasing humidity. When subjected to relative humidity of a predetermined percent, the paper color will change from blue to pink. The composition of the strip sections is varied to provide a graduated humidity scale with the point of change being the humidity of the atmosphere or material being measured. A separate table is provided with directions for use which includes a plurality of rows and columns having various graduated values of ambient relative humidity (ARH) or equilibrium relative humidity (ERH) for the air or paper. Temperatures are shown in a vertical axis along one side of the table and percent humidity in a horizontal axis at the bottom of the table, with the intersection of the temperature and humidity scales providing the relative humidity value of the air or paper being measured. A second table is provided indicating a range of differences in moisture between the paper and air readings which can effect various printing conditions and directions for corrective actions in order to avoid possible difficulties.

Other objects and advantages will become apparent from the following description in conjunction with the accompanying drawings.

DESCRIPTION OF THE PREFERRED EMBODIMENT

Figures 1, 2, 3:
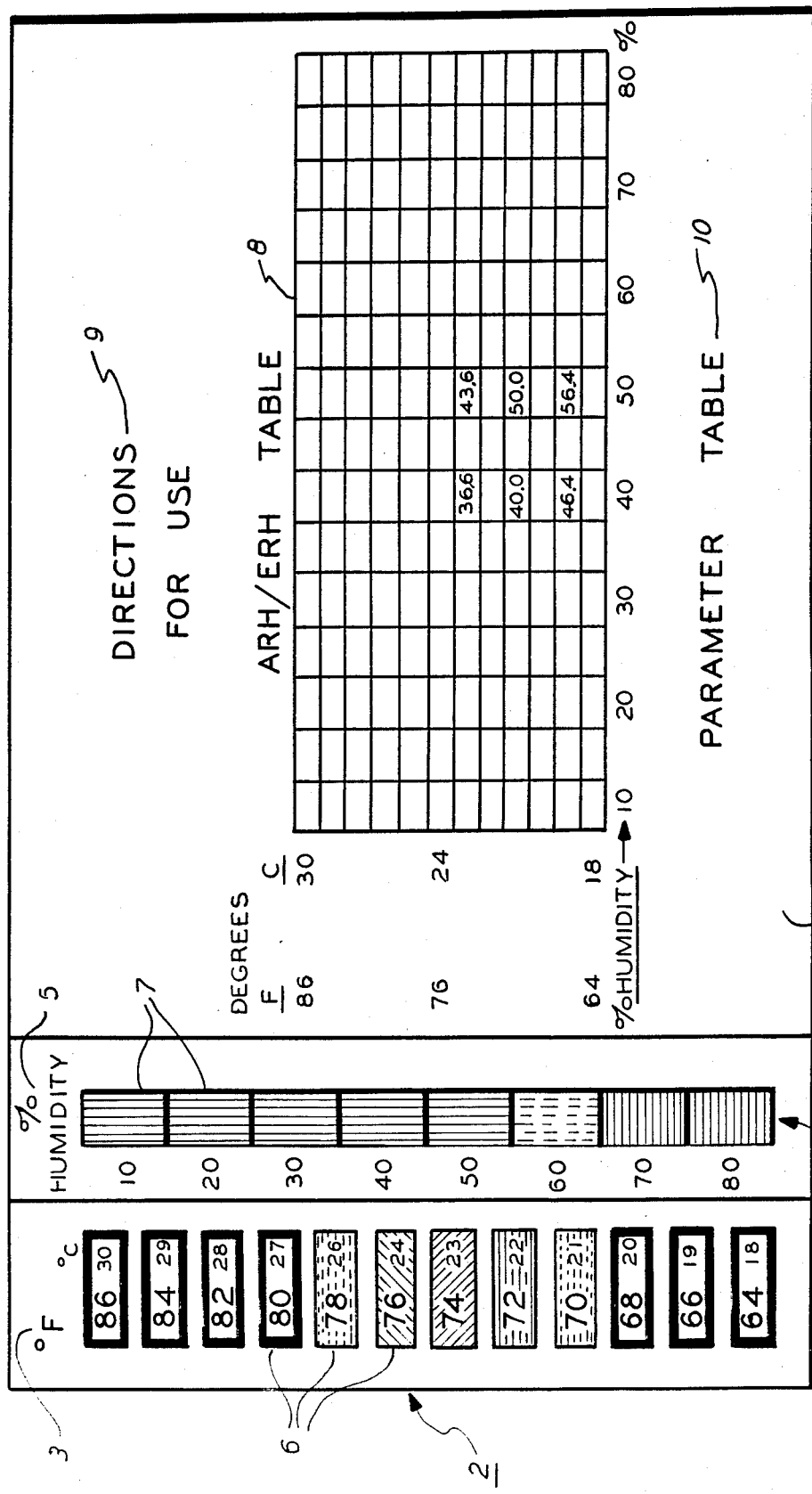
FIG. 1 is a plan view of one embodiment of the invention showing the temperature and humidity sensor scales, a table of ERH and ARH values for various temperature and humidity conditions, directions for use, and a parameter table of differences between relative humidity values with effects on various printing conditions.
FIG. 2 is a side view in partial cross-section of the temperature scale including a plurality of thermochromic liquid crystal sensors on a plastic sheet.
FIG. 3 is a side view in partial cross-section of the humidity scale, including a plurality of paper strip sections impregnated with inorganic salt compositions which change color with humidity, secured on the same plastic sheet.

As shown in FIG. 1, a flexible sheet 1 of a suitable plastic or paper material serves as a backing to which are secured a first temperature scale 2, graduated in °F. or °C., as indicated at 3, and a second humidity scale 4, graduated in % humidity as indicated at 5. The temperature scale includes a series of encapsulated liquid crystals 6, each sensitive to the individual temperature indicated from 64° to 86° F. The crystals are normally black or gray and brighten to green at the room temperature, which in this case is shown at the 74° F. crystal. The next lower crystal 72° F. would be a dark blue color and the next higher crystal 76° F. would be brown at the 74° F. room temperature. The entire scale has a plastic cover.

The humidity scale includes a plurality of exposed paper strips 7 impregnated with an inorganic salt composition which changes color with humidity. The colors vary from a bright blue at a high humidity scale of 80% to lighter blue, lavender, and then pink at the humidity of the room air being measured. In this case, the 50% humidity strip is the first to indicate a pink color. The strips indicating 40 to 10% humidity will also be pink, with the first strip at which the color changes to pink being the measured humidity. The temperature and % humidity scales are used as the vertical and horizontal axes respectively for determining the % ambient relative humidity, ARH, of the air surrounding the paper to be processed and the equilibrium relative humidity, ERH, of the paper. Table 8 contains the ARH/ERH figures listed in the outlined rows and columns. A typical example of the ARH figure obtained from the table would be that at the intersection of the 74° F. measured room temperature along the vertical axis and the 50% measured room humidity along the horizontal axis which is indicated as 43.6.

Figure 4:
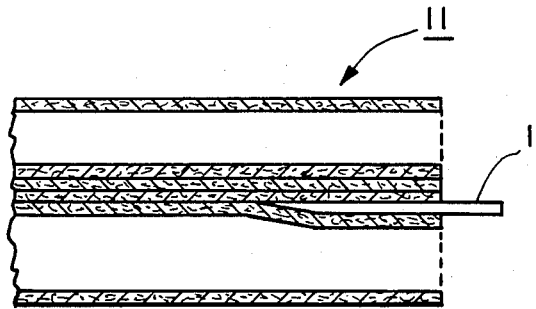
FIG. 4 is a side view in partial cross-section of a sack of paper sheets with the indicator device inserted therein.

Each figure in the table is obtained from an established formula taken from tests made by the German Research Institute for Printing and Reproduction Techniques, known as FOGRA. The humidity of 50% and a temperature of 70° F. are used as a reference with an ARH of 50.0 being indicated at the intersection of those two figures. The difference in temperature above 70° F. is multiplied by a factor of 1.6 and then subtracted from 50 to obtain the figures at the appropriate intersections of the table. Thus, 74° F.−70° F.=4×1.6=6.4 and 50−6.4=43.6. When the measured temperature is below 70° F., the same formula is used but the multiplied factor is then added to 50. Thus, 70° F.−66° F.=4×1.6=6.4 and 50+6.4=56.4. A like calculation is made for a measured humidity of 40% with an ARH figure of 40.0 at the intersection with 70° F. The ARH at 74° F. and 40% humidity is thus 4×1.6=6.4 and 40−6.4=33.6 as indicated, while at 66° F., the figure is 40+6.4=46.4. The same extrapolations are made throughout the table to provide the corresponding figures. Like calculations apply to the ERH figures which are obtained from the temperature and humidity measurements taken by inserting the scales into the paper stack or roll 11 as shown in FIG. 4.

The complete ARH/ERH table 8 is as follows:

| DEGREES F. | C. | ARH/ERH TABLE | | | | | | | | | | | | | | |
|---|---|---|---|---|---|---|---|---|---|---|---|---|---|---|---|---|
| 86 | 30 | | | | | 4.4 | 9.4 | 14.4 | 19.4 | 24.4 | 29.4 | 34.4 | 39.4 | 44.4 | 49.4 | 54.4 |
| 84 | 29 | | | | 2.6 | 7.6 | 12.6 | 17.6 | 22.6 | 27.6 | 32.6 | 37.6 | 42.6 | 47.6 | 52.6 | 57.6 |
| 82 | 28 | | | 0.8 | 5.8 | 10.8 | 15.8 | 20.8 | 25.8 | 30.8 | 35.8 | 40.8 | 45.8 | 50.8 | 55.8 | 60.8 |
| 80 | 27 | | | 4.0 | 9.0 | 14.0 | 19.0 | 24.0 | 29.0 | 34.0 | 39.0 | 44.0 | 49.0 | 54.0 | 59.0 | 64.0 |
| 78 | 26 | | 2.2 | 7.2 | 12.2 | 17.2 | 22.2 | 27.2 | 32.2 | 37.2 | 42.2 | 47.2 | 52.2 | 57.2 | 62.2 | 67.2 |
| 76 | 24 | 0.4 | 5.4 | 10.4 | 15.4 | 20.4 | 25.4 | 30.4 | 35.4 | 40.4 | 45.4 | 50.4 | 55.4 | 60.4 | 65.4 | 70.4 |
| 74 | 23 | 3.6 | 8.6 | 13.6 | 18.6 | 23.6 | 28.6 | 33.6 | 38.6 | 43.6 | 48.6 | 53.6 | 58.6 | 63.6 | 68.6 | 73.6 |
| 72 | 22 | 6.8 | 11.8 | 16.8 | 21.8 | 26.8 | 31.8 | 36.8 | 41.8 | 46.8 | 51.8 | 56.8 | 61.8 | 66.8 | 71.8 | 76.8 |
| 70 | 21 | 10.0 | 15.0 | 20.0 | 25.0 | 30.0 | 35.0 | 40.0 | 45.0 | 50.0 | 55.0 | 60.0 | 65.0 | 70.0 | 75.0 | 80.0 |
| 68 | 20 | 13.2 | 18.2 | 23.2 | 28.2 | 33.2 | 38.2 | 43.2 | 48.2 | 53.2 | 58.2 | 63.2 | 68.2 | 73.2 | 78.2 | 83.2 |
| 66 | 19 | 16.4 | 21.4 | 26.4 | 31.4 | 36.4 | 41.4 | 46.4 | 51.4 | 56.4 | 61.4 | 66.4 | 71.4 | 76.4 | 81.4 | 86.4 |
| 64 | 18 | 19.6 | 24.6 | 29.6 | 34.6 | 39.6 | 44.6 | 49.6 | 54.6 | 59.6 | 64.6 | 69.6 | 74.6 | 79.6 | 84.6 | 89.6 |
| | | 10 | 15 | 20 | 25 | 30 | 35 | 40 | 45 | 50 | 55 | 60 | 65 | 70 | 75 | 80 |
| | | | | | | | | % HUMIDITY | | | | | | | | |

The following directions for use are printed in area 9 of the paper sheet 1, which may be in the form of a separate card with the directions and table printed thereon. The temperature and % humidity scales would then be secured on a separate sheet for measuring the ambient and paper stack conditions. The sheet with the scales may be part of a plastic folder having pockets to hold the card and the complete unit may be supplied to the printer as an attachment to the paper stack, at little or no cost.

DIRECTIONS

Place the temperature and humidity indicators near the unopened load of paper to be printed. Wait at least 15 minutes before reading the temperature as indicated by the bright green colored area on the temperature scale. If no green color is evident, read the brown colored area. If the indicator remains black, the temperature is either higher or lower than the indicator can sense. In that case, immediately contact the paper supplier technical representatives on how best to proceed.

Next, read the humidity indicator by locating the lowermost all pink segment of the indicator strip. The adjacent number will be the % humidity reading unless the segment immediately below shows a lavender color.

In that case, add 5% to the number adjacent the noted pink segment.

Now, locate the point on the ARH/ERH table at which the temperature and humidity readings intersect. That figure is the approximate ARH of the surrounding air. To read the ERH of the paper, unwrap the load and insert the sheet with the scales into the paper stack between sheets near the center about 2 inches down from the top. Wait at least 15 minutes and remove to read in the same manner as above for the ARH. The intersection of the two readings will now be the approximate ERH of the paper. Take the percentage difference between the ARH and ERH and refer to the Parameter Table 10 to determine whether there might be wrinkling or registration problems in printing on this paper in view of the ARH of the surrounding air. If so, follow the parameter table directions below for corrective measures and notify the technical representative.

PARAMETER TABLE

Below are approximate parameters of allowable differences in humidity for various kinds of printing before registration problems will become apparent. If the table indicates possible problems can occur, the pressroom ARH should be changed to more closely approximate the ERH of the paper. If this is not possible, the open paper load should be covered with plastic to limit moisture absorption when not printing.

| If the Nature of Printing Is: | The % Difference Must be Within: |
| --- | --- |
| 1. No register, one pass | 12% dry or 8% moist |
| 2. Commercial register, one pass multicolor press | 8% dry or 12% moist |
| 3. Close register, one pass multicolor press | 5% dry or 8% moist |
| 4. Commercial register, two or more passes | 4% dry or 8% moist |
| 5. Close register, two or more passes | 0% dry or 8% moist |

The percent difference figures refer to the difference in relative humidity and whether the air is more dry or more moist than the paper. In the first case, if the air is more than 12% drier or over 8% more moist than the paper, wrinkling, distortion and registration problems may result. For printing requiring close registration and multiple passes, the problems created by these differences become more critical.

The present invention thus provides a simple, inexpensive device for determining relative humidity differences between the paper to be printed and the surrounding air in order to avoid problems during printing.

While only a single embodiment has been illustrated and described, it is apparent that many variations may be made in the particular design and configuration without departing from the scope of the invention as set forth in the appended claims.

What is claimed is:

1. A relative humidity indicating device for measuring relative humidity of paper sheets and the surrounding air comprising:
   a first thin flat strip including temperature sensing means providing a graduated temperature scale for measuring the temperature of sheets of papers and the ambient air surrounding said paper;
   a second thin flat strip including humidity sensing means providing a graduated humidity scale for measuring the humidity of said paper and the ambient air surrounding said paper;
   a thin flat sheet supporting and securing said first and second strips thereon; and
   thin flat tabular means having printed rows and columns of predetermined figures indicative of relative humidity values of said paper and ambient air, a first axis of said tabular means having a graduated temperature scale corresponding to that of said first strip and a second axis having a graduated humidity scale corresponding to that of said second strip with the intersection of measured readings from said temperature and humidity scales for said paper and for said ambient air representing the respective relative humidity values of said paper and said ambient air.

2. The device of claim 1 wherein said paper is in the form of stacked sheets or a roll adapted for printing thereon.

3. The device of claim 2 wherein said temperature sensing means is a plurality of liquid crystals sensitive to predetermined temperatures and changing colors with temperature to provide said graduated scale in degrees.

4. The device of claim 3 wherein said humidity sensing means is a plurality of inorganic salt impregnated paper segments sensitive to predetermined humidities and changing colors with humidity to provide said graduated scale in percent humidity.

5. The device of claim 4 wherein said tabular means figures indicate percent equilibrium relative humidity of the paper and percent ambient relative humidity of the surrounding air.

6. The device of claim 5 wherein said thin flat sheet having said strips thereon is insertable between said paper sheets or into said roll to measure the temperature and humidity of said paper and is exposed to said surrounding air to measure the temperature and humidity of said air.

7. The device of claim 6 wherein said tabular means includes a sheet of paper having said figures printed thereon providing a first table and directions for use of said table printed thereon.

8. The device of claim 7 including a second table printed on said sheet of paper including a list of ranges of maximum differences in moisture between the paper to be printed on and said surrounding air for avoidance of printing problems under varying printing conditions.

9. The device of claim 8 wherein said second table includes directions for correction of printing problems.

10. The device of claim 9 wherein said thin flat sheet is plastic, said first and second strips being secured on adjacent areas of said plastic sheet.

* * * * *